US00PP11371P

United States Patent [19]

Dubois et al.

[11] Patent Number: Plant 11,371

[45] Date of Patent: May 2, 2000

[54] SHRUB ROSE PLANT NAMED 'IVTAGOLF'

[75] Inventors: L. A. M. Dubois, Wageningen; D. P. de Vries, Ede, both of Netherlands

[73] Assignee: Stichting DLO-Centrum voor Plantenveredelings- en Reproduktieonderzoek, Wageningen, Netherlands

[21] Appl. No.: 09/079,738

[22] Filed: May 15, 1998

[51] Int. Cl.[7] ..... A01H 5/00

[52] U.S. Cl. ..... Plt./103

[58] Field of Search ..... Plt./101, 103

*Primary Examiner*—Howard J. Locker
*Attorney, Agent, or Firm*—Webb Ziesenheim Logsdon Orkin & Hanson, P.C.

[57] ABSTRACT

The new cultivar is a variety of shrub rose plant having a broad bushy growth habit. The single flowers are very small to small and white in color.

2 Drawing Sheets

BACKGROUND OF THE NEW PLANT

This discovery relates to a new and distinct variety of shrub rose plant identified by the varietal name of 'Ivtagolf'. The new variety was discovered in a selected breeding program at Stichting DLO-Centrum voor Plantenveredelings- en Reproduktieonderzoek (CPRO-DLO) in Wageningen, The Netherlands in 1984. The goal of the breeding program was to develop cultivars of pot roses and patio roses. The new variety is a selection from the crossing of unnamed varieties of *R. multiflora* and *R. elegantula.*

The first asexual reproduction took place at Stichting DLO-Centrum voor Plantenveredelings- en Reproduktieonderzoek (CPRO-DLO) in Wageningen, The Netherlands in 1990 and the new variety has been propagated by cutting, stenting and grafting on *R. dumetorum* 'laxa'. Continued observations from the vegetative cuttings have confirmed that the distinguishing features of the new variety remain stable and are retained through successive propagations.

DESCRIPTION OF THE DRAWING

The accompanying photographic drawings illustrate the new variety, with the color being as nearly true as is possible with color illustrations of this type. Sheet 1 illustrates the overall plant habit of the new cultivar and Sheet 2 illustrates a close-up view of the bloom and foliage of the new cultivar.

DESCRIPTION OF THE NEW PLANT

The following detailed descriptions set forth the characteristics of the new variety. The data which define these characteristics were collected from asexual reproductions carried out at Stitchting DLO-Centrum voor Plantenveredelings- en Reproduktieonderzoek (CPRO-DLO) in Wageningen, The Netherlands. Color references are primarily to the R.H.S. Colour Chart of The Royal Horticultural Society of London.

PLANT

Varietal Name: Ivtagolf.
Commercial name: Golf.
Botanical name: *Rosa l.*
Size:
- *Height.*—80–100 cm.
- *Width.*—60–80 cm.

Habit: Shrub.
Growth vigor: Vigorous.

Wood color: Green Group 137C.
Thorns:
- *Color.*—Yellow-Green Group 151A.
- *Size.*—About 0.6 cm long.
- *Shape.*—Concave.
- *Location on stem and branches.*—About equal number of thorns on the main canes from the base and on the lateral branches; very few in number.

Disease resistance: Under normal outdoor climate and weather conditions with no long periods of coldness, dryness, or wetness, resistant to black spot and mildew.

FOLIAGE

Arrangement: Compound.
Compound leaf size: 8.0 by 7.0 cm.
Leaflets:
- *Number on typical stem leaves.*—7–9.
- *Size.*—Small, about 3.5 by 2.0 cm.
- *Color.*—Upper surface: Yellow-Green Group 147A. Lower surface: Yellow-Green Group 146A.
- *Shape.*—Ovate.
- *Texture.*—Upper side, glossy.
- *Margin.*—Single, small serrations.
- *Petiole rachis.*—Color: Yellow-Green Group 146C. Texture: Rough, with glands along the side.
- *Stipules.*—Serrated.

BUDS

Size: About 0.8 cm by 0.7 cm.
Shape: Short, ovate.
Color: Yellow-Green Group 144A.
Color changes during opening: None.
Sepals:
- *Arrangement.*—Slightly foliated.
- *Color.*—Upper surface: Green Group 138B. Lower surface: Yellow-Green Group 144A.
- *Texture.*—Sparsely covered with fine hairs.

Receptacle:
- *Color.*—Yellow-Green Group 144A.
- *Shape.*—Pear shaped, about 0.3 cm by 0.6 cm.
- *Texture.*—Smooth.

Peduncle:
- *Color.*—Yellow-Green Group 144A.
- *Length.*—3 cm (average).
- *Strength.*—Stiff, erect.
- *Texture.*—Smooth.

FLOWER

Borne: 50–60 per cluster.
Size: 3.5–4.0 cm in diameter.
Form: Single flowered, flat.
Petals:
*Number per floret.*—5.
*Color.*—Upper surface: White. Lower surface: White. Color changes with maturity: None.
*Texture.*—Thick.
*Size.*—About 1.5 cm by 1.0 cm.
*Shape.*—Heart shaped.
*Arrangement.*—Imbricated.
Persistence: Petals drop off cleanly.
Lastingness: 3–5 days.
Fragrance: None.
Blooming period: Long, recurrent flowering.

REPRODUCTIVE ORGANS

Stamens:
*Number.*—75–90 per flower.
*Anther.*—Length: About 1.0 mm. Color: Yellow-Orange Group 15A. Pollen color: Yellow-Orange Group 15B.
*Filament.*—Length: About 5 mm. Color: Yellow-Orange Group 15C.
Pistils:
*Number.*—20–25 per flower.
*Style.*—Color: Green-Yellow Group 1C. Length: About 0.7 cm.
*Stigma.*—Color: Green-Yellow Group 1B. Length: About 1.0 mm.

We claim:

1. A new and distinct variety of rose plant substantially as shown and described.

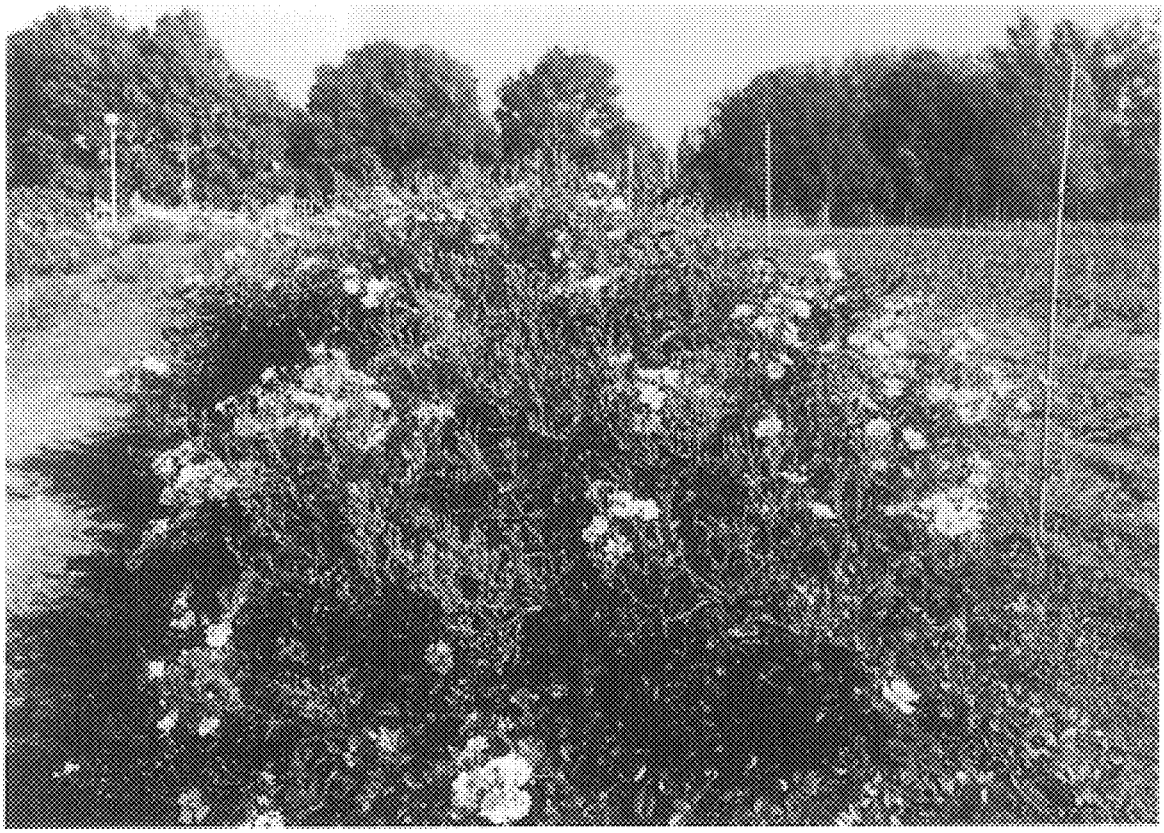

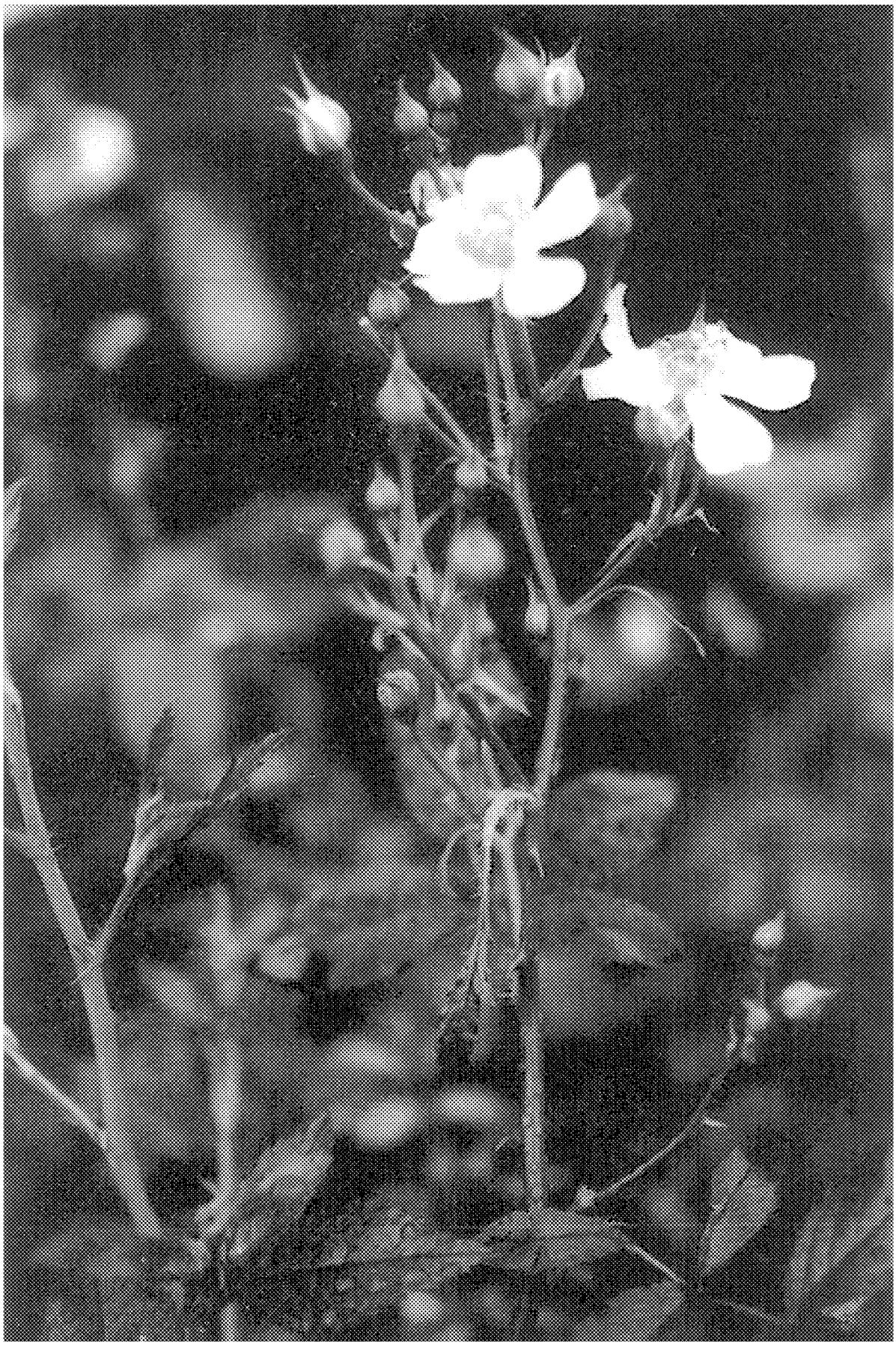

* * * * *